United States Patent
Lee (10) Patent No.: US 9,974,628 B2
(45) Date of Patent: May 22, 2018

(54) TOOTH CLEANING DEVICE HAVING INTERNAL FLUID CONDUIT FORMED THEREIN

(71) Applicant: Bluereo Inc., Seoul (KR)

(72) Inventor: Seung Min Lee, Seoul (KR)

(73) Assignee: Bluereo Inc., Seoul (KR)

( * ) Notice: Subject to any disclaimer, the term of this patent is extended or adjusted under 35 U.S.C. 154(b) by 0 days. days.

(21) Appl. No.: 15/305,981

(22) PCT Filed: Nov. 6, 2015

(86) PCT No.: PCT/KR2015/011919
§ 371 (c)(1),
(2) Date: Oct. 21, 2016

(87) PCT Pub. No.: WO2016/133265
PCT Pub. Date: Aug. 25, 2016

(65) Prior Publication Data
US 2017/0042638 A1  Feb. 16, 2017

(30) Foreign Application Priority Data
Feb. 16, 2015  (KR) ........................ 10-2015-0023293

(51) Int. Cl.
*A61C 1/00* (2006.01)
*A46B 7/04* (2006.01)
(Continued)

(52) U.S. Cl.
CPC ............ *A61C 1/0061* (2013.01); *A46B 7/042* (2013.01); *A46B 9/04* (2013.01); *A46B 11/002* (2013.01);
(Continued)

(58) Field of Classification Search
CPC combination set(s) only.
See application file for complete search history.

(56) References Cited

U.S. PATENT DOCUMENTS 7,004,662 B1 *  2/2006  Gordon .............. A46B 11/0017
401/180
2007/0041779 A1 *  2/2007  Kuo ................... A46B 11/0058
401/188 R
(Continued)

FOREIGN PATENT DOCUMENTS

KR   20-0326536 Y1   9/2003
KR   20-0374492 Y1   1/2005
(Continued)

*Primary Examiner* — David Walczak
(74) *Attorney, Agent, or Firm* — Novick, Kim & Lee, PLLC; Sang Ho Lee (57) ABSTRACT

A tooth cleaning device having an internal fluid conduit formed therein, and the tooth cleaning device includes: a main body which has a tube provided in the main body and selectively connectable with a drive unit; and a cleaning body which is assembled to one side of the main body, and has the internal fluid conduit formed in the cleaning body and connectable with the tube, in which at least one nozzle is formed to be opened at one end of the internal fluid conduit. Further, when the main body and the cleaning body are assembled, one end of the tube is connected to one end of the internal fluid conduit so as to form a single continuous flow path, and through the single continuous flow path, a cleaning solution may be discharged or a fluid is sucked and then discharged to the outside.

14 Claims, 9 Drawing Sheets

(51) Int. Cl.
  *A61C 17/02* (2006.01)
  *A61C 17/028* (2006.01)
  *A46B 9/04* (2006.01)
  *A46B 11/00* (2006.01)
  *A46B 15/00* (2006.01)
  *A61C 1/08* (2006.01)
  *A61C 17/22* (2006.01)
  *A46B 11/06* (2006.01)

(52) U.S. Cl.
  CPC ........ *A46B 11/0006* (2013.01); *A46B 11/063* (2013.01); *A46B 15/0036* (2013.01); *A61C 1/00* (2013.01); *A61C 1/088* (2013.01); *A61C 17/02* (2013.01); *A61C 17/0202* (2013.01); *A61C 17/0208* (2013.01); *A61C 17/028* (2013.01); *A61C 17/22* (2013.01); *A46B 7/046* (2013.01)

(56) References Cited

U.S. PATENT DOCUMENTS

2009/0017423 A1  1/2009  Gottenbos et al.
2009/0136285 A1* 5/2009  Hall ................... A61C 17/222
                                                        401/282

FOREIGN PATENT DOCUMENTS

KR  10-1059622 B1  8/2011
KR  10-1255575 B1  4/2013

* cited by examiner

TOOTH CLEANING DEVICE HAVING INTERNAL FLUID CONDUIT FORMED THEREIN

BACKGROUND

This application is prepared under the Research and Business Development program, which is funded by the Ministry of Trade, Industry and Energy (N002012), Republic of Korea.

Field

The present disclosure relates to a tooth cleaning device, and more particularly, to a tooth cleaning device capable of supplying a cleaning solution or discharging a fluid in the mouth to the outside through a flow path formed in the tooth cleaning device.

Description of the Related Art

The most typical tool for cleaning teeth is a toothbrush, and the toothbrush is a tool used to clean the teeth with toothpaste attached to the toothbrush for the purpose of health care, hygiene, and cleanliness for the teeth. The toothbrush includes a handle portion formed in the form of a stick, and a brush formed by densely planting thin bristle members on a body formed at a tip of the handle portion.

Further, when cleaning the teeth, a user attaches the brush of the toothbrush onto the teeth and repeatedly performs an operation of removing gargling water in the mouth while rubbing the teeth, and after brushing the teeth, the user washes the interior of the mouth with cleaning water, and then spits out the gargling water.

In addition to the toothbrush in the related art having a traditional structure, recently, a tooth cleaning device for supplying a cleaning solution has been developed and used. The tooth cleaning device supplies a high-pressure cleaning solution such as water into the mouth in order to clean the teeth or the interdental spaces, but in the case of the aforementioned tooth cleaning device, a nozzle for spraying the cleaning solution cannot be replaced or a problem of waterproof performance occurs when the nozzle is disassembled in most instances.

Therefore, there is a need for a tooth cleaning device which may allow only a nozzle and some components of the tooth cleaning device to be replaced, allow maintenance to be conveniently performed on the interior of the tooth cleaning device, and have excellent waterproof performance.

SUMMARY

The present disclosure has been made in an effort to solve the aforementioned problems in the related art, and to enable components of a nozzle to be easily assembled to and disassembled from a tooth cleaning device, and enable waterproof performance to be maintained after the components are assembled.

According to an aspect of the present disclosure, there is provided a tooth cleaning device having an internal fluid conduit formed therein, the tooth cleaning device including: a main body which has a tube provided in the main body and selectively connectable with a drive unit; and a cleaning body which is assembled to one side of the main body, and has the internal fluid conduit formed in the cleaning body and connectable with the tube, wherein at least one nozzle is formed to be opened at one end of the internal fluid conduit, in which when the main body and the cleaning body are assembled, one end of the tube is connected to one end of the internal fluid conduit so as to form a continuous flow path.

Further, a coupling protrusion and a coupling channel, which correspond to each other, may be formed on the cleaning body and the main body, respectively, such that during a process in which the cleaning body is coupled to the main body, the coupling protrusion is guided along the coupling channel and then caught and fixed by one side of the coupling channel.

A flange may be separably coupled to the main body, the coupling channel may be formed to be recessed in an inner surface of the flange, the coupling channel may include an introduction portion which has one end opened to the outside, a connecting portion which extends from the introduction portion in a direction in which the main body and the cleaning body are coupled, and a rotation portion which extends from the connecting portion in a direction in which the rotation portion is orthogonal to or inclined from the connection portion, and a catching projection may protrude at one end of the rotation portion.

Further, the tube may be provided in the main body so as to be separable from the main body, and the internal fluid conduit may be formed integrally with the cleaning body.

One end of the tube provided in the main body may be positioned in the flange, such that when the cleaning body is coupled to the flange, one end of the internal fluid conduit of the cleaning body and one end of the tube are connected to each other.

Meanwhile, a tube guide may be provided below the flange, the tube guide may include a guide plate which is supported and fixed on an inner surface of the main body, a tube coupling portion which protrudes from a bottom surface of the guide plate and is coupled to one end of the tube, and a conduit insertion portion which protrudes from an upper surface of the guide plate and is positioned in the flange, and when the cleaning body is coupled to the flange, at least a part of the conduit insertion portion may be inserted into the internal fluid conduit of the cleaning body.

A waterproof seal may be provided on an outer surface of the conduit insertion portion.

Further, the tube coupling portion may be formed such that a width thereof is decreased toward the protruding one end, and at least one coupling rib may protrude on an outer surface of the tube coupling portion.

In addition, a light emitting unit, which emits light, may be provided in the main body, and an evading portion may be formed in the tube guide by being recessed or opened so as to allow light emitted from the light emitting unit to pass through the evading portion or allow the light emitting unit to be seated on the evading portion.

Here, the cleaning body may include: a connecting bar which has the internal fluid conduit formed therein; a cleaning head which is provided at one end of the connecting bar and has at least one nozzle formed on an outer surface thereof; and a coupling boss which protrudes from the other end of the connecting bar and has a coupling protrusion provided on an outer surface thereof.

The cleaning head may be formed in a cylindrical shape, a plurality of nozzles may be formed on at least one of an outer circumferential surface, an upper surface, or a bottom surface of the cleaning head, and the nozzle may be formed radially toward an outer circumferential surface of the cleaning head.

In addition, a brush may be separably coupled to the cleaning head.

The tube may be provided in the main body so as to be separable from the main body, and the drive unit may supply a washing liquid to the tube, or suck a liquid from the nozzle by providing negative pressure to the tube.

According to the tooth cleaning device having the internal fluid conduit formed therein according to the present disclosure, the following effects can be expected.

According to the present disclosure, since the main body and the cleaning body, which constitute the tooth cleaning device, may be assembled and disassembled, it is possible to repair, replace, or wash some components such as the tube and the internal fluid conduit by disassembling the components, thereby improving maintainability of the tooth cleaning device.

Further, according to the present disclosure, since the main body and the cleaning body may be easily assembled and disassembled through a rotational operation, and one end of the tube and the internal fluid conduit of the cleaning body are naturally connected through the tube guide during this assembling process, assembly property is improved, and since the waterproof seal of the tube guide is compressed by the internal fluid conduit during the process in which the main body and the cleaning body are assembled, a waterproof function is implemented without performing separate work, and as a result, operational reliability may be improved.

In addition, according to the present disclosure, since the brush is selectively coupled to the cleaning head, the user may use the tooth cleaning device only for supplying or discharging the cleaning solution after eliminating the brush, or may use the tooth cleaning device like a typical toothbrush after coupling the brush, and as a result, utilization of the tooth cleaning device is improved.

DETAILED DESCRIPTION OF THE EMBODIMENT

Hereinafter, some exemplary embodiments of the present disclosure will be described in detail with reference to the illustrative drawings. When reference numerals refer to constituent elements of each drawing, it should be noted that although the same constituent elements are illustrated in different drawings, the same constituent elements are referred to by the same reference numerals as possible. Further, in the following description of the exemplary embodiments of the present disclosure, a detailed description of publicly known configurations or functions incorporated herein will be omitted when it is determined that the detailed description hinders the understanding of the exemplary embodiments of the present disclosure.

In addition, the terms first, second, A, B, (a), and (b) may be used to describe constituent elements of the exemplary embodiments of the present disclosure. These terms are used only for the purpose of discriminating one constituent element from another constituent element, and the nature, the sequences, or the orders of the constituent elements are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

Figure 1:
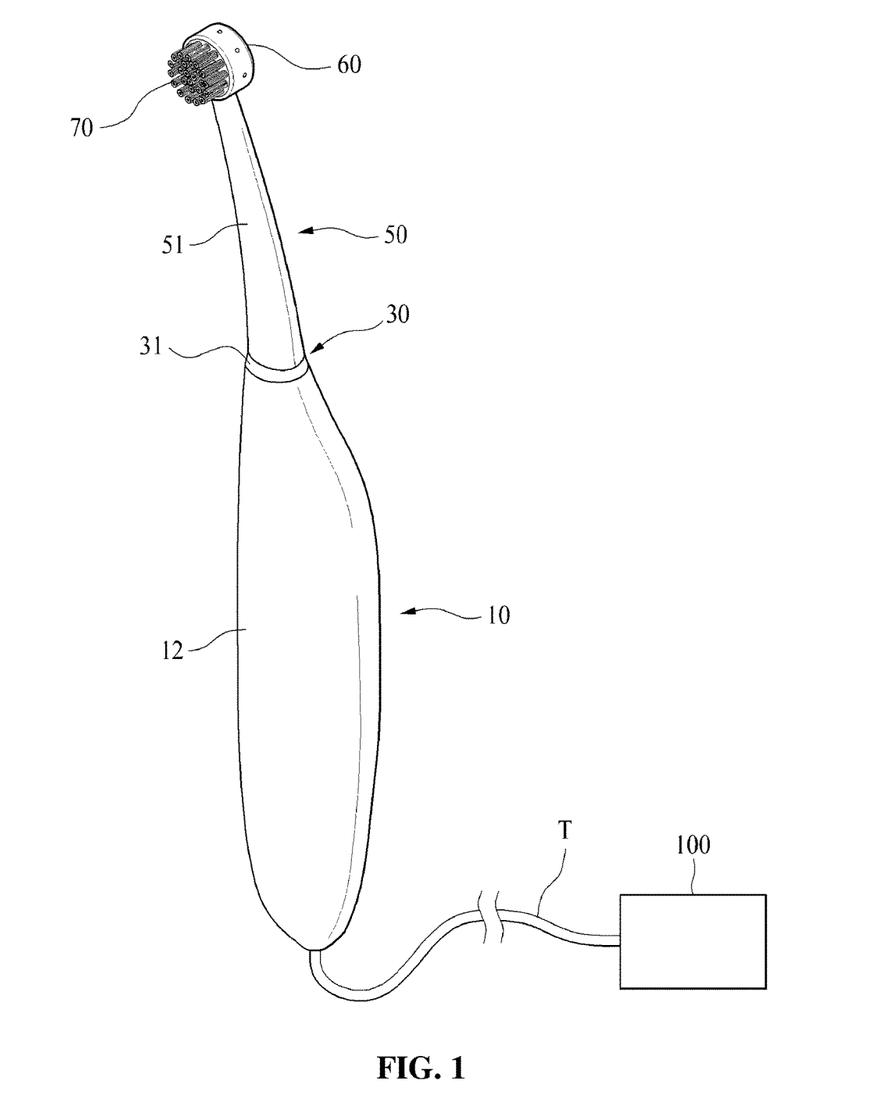
FIG. 1 is a perspective view illustrating a configuration of an exemplary embodiment of a tooth cleaning device having an internal fluid conduit according to the present disclosure.

FIG. 1 illustrates a perspective view illustrating a configuration of an exemplary embodiment of a tooth cleaning device having an internal fluid conduit according to the present disclosure.

As illustrated in FIG. 1, a tooth cleaning device having an internal fluid conduit 58 formed therein according to the present disclosure (hereinafter, referred to as a 'tooth cleaning device') broadly includes a main body 10 and a cleaning body 50. The main body 10 defines a framework and an external shape of a lower portion of the tooth cleaning device, and is a kind of a handle portion substantially grasped by a user when the user uses the tooth cleaning device, and the cleaning body 50 is a portion used to clean teeth.

Further, as described again below, a drive unit 100 is connected to the tooth cleaning device, and the drive unit 100 is a part for generating external force for supplying a cleaning solution through a tube T1 or sucking a fluid in the mouth. For reference, in the present exemplary embodiment, the drive unit 100 is configured as an external main body provided outside the tooth cleaning device, but the drive unit 100 may be configured integrally with the tooth cleaning device. For example, the drive unit 100 may be a component mounted in the main body 10, or a component coupled to the main body 10.

Hereinafter, these structures will be sequentially described. First, the main body 10 has a kind of a bar shape having a vacant interior, and the main body 10 is a portion grasped by the user. In the present exemplary embodiment, as illustrated in FIG. 1, an outer surface 12 of the main body 10 is formed as a curved surface, but may be formed to have various external shapes such as a polygonal shape or a recessed shape so as to indicate a portion grasped by the user.

An internal space is formed in the main body 10. The internal space extends and elongates in a longitudinal direction of the main body 10, and the tube T1 and a tube guide 40, which will be described below, are inserted into the internal space.

Figure 5:
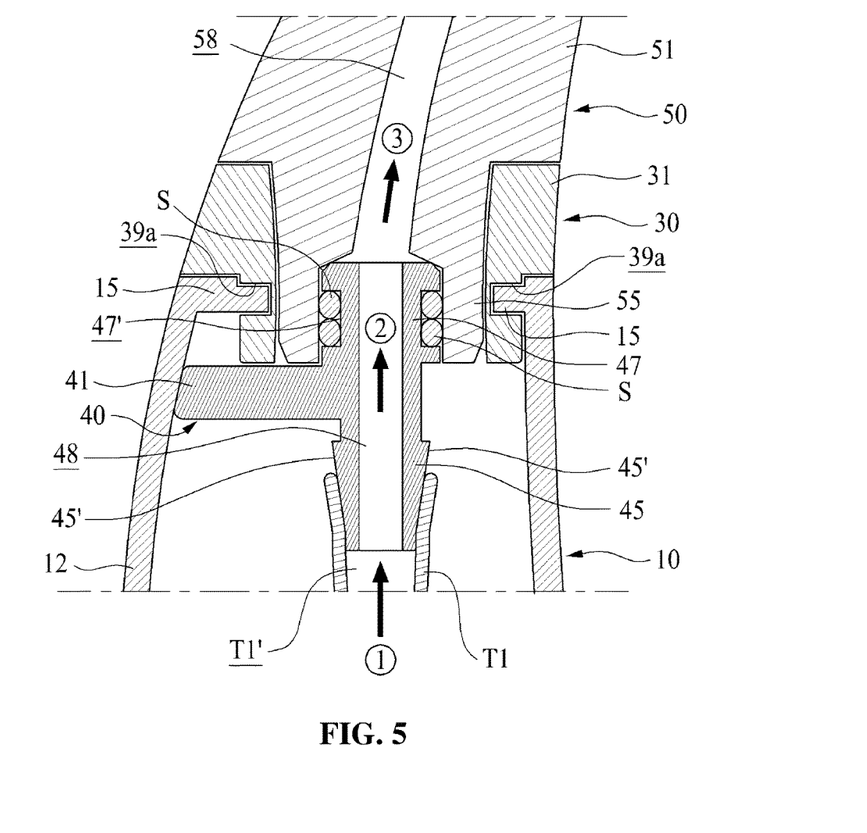
FIG. 5 is a cross-sectional view illustrating configurations of the cleaning body, the flange, and the tube guide that constitute the exemplary embodiment of the present disclosure.

As illustrated in FIG. 5, first fastening protruding portions 15 are formed at one side of the main body 10. The first fastening protruding portions 15 correspond to second fastening recesses 39*a* of the flange 30 which will be described below, and as the first fastening protruding portions 15 are inserted into the second fastening recesses 39a of the flange 30, the main body 10 and the flange 30 are coupled to each other. Of course, fastening grooves may be formed in the main body 10, and fastening protruding portions may be provided on the flange 30.

For reference, the main body 10 may be configured as two components, and the two components are coupled to each other with the flange 30 being disposed between the two components, such that the flange 30 may be coupled to the main body 10.

The tube T1 is inserted into the main body 10. The tube T1 extends in the longitudinal direction of the main body 10, one end of the tube T1 is connected to an internal fluid conduit 58 of the cleaning body 50 which will be described below, and the other end of the tube T1 is connected with the drive unit 100. Therefore, the tube T1 may transmit negative pressure, which is produced by suction power of the drive unit 100, to the cleaning body 50, or on the contrary, the tube T1 may transmit the cleaning solution, which is discharged by discharge power of the drive unit 100, to the cleaning body 50.

One end of the tube T1 is coupled to a tube coupling portion 45 of the tube guide 40 which will be described below, and in the present exemplary embodiment, as illustrated in FIG. 5, one end of the tube T1 is elastically deformed in a direction in which a width thereof is increased, and then coupled to the tube coupling portion 45 in a press-fit manner. Further, the other end of the tube T1 is separably connected with the drive unit 100.

As described above, in the present exemplary embodiment, both ends of the tube T1 are separably coupled to the tube guide 40 and the drive unit 100, respectively, and as a result, the user may easily perform maintenance such as operations of separating and replacing the tube T1 or reassembling the tube T1 after washing the tube T1. Of course, the tube T1 may be integrally formed in the main body 10, or the tube T1 may be configured such that at least a part of the tube T1 is formed integrally with the main body 10 and the remaining part of the tube T1 is connected to the main body 10. For reference, in the drawings, the tube is described by using the tube T connected to the drive unit 100 and the tube T1 provided in the main body 10, but the tube T and the tube T1 may be configured by extending a single tube.

Although not illustrated, an operating unit may be provided on the outer surface of the main body 10. The operating unit may be a kind of a switch for operating the drive unit 100, and a light emitting unit to be described below may be manipulated by the operating unit.

The flange 30 may be coupled to one end of the main body 10. The flange 30 is coupled to an upper portion of the main body 10, and serves to connect the main body 10 and the cleaning body 50. More exactly, as the cleaning body 50 is coupled to the flange 30, the cleaning body 50 and the main body 10 are connected to each other.

Figure 2:
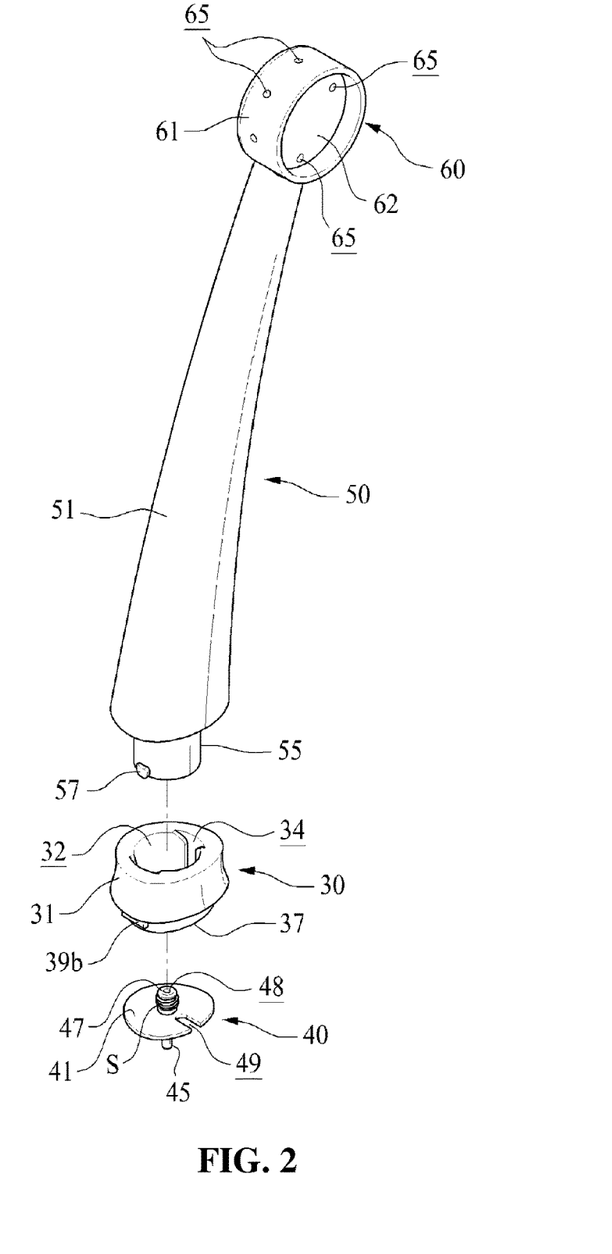
FIG. 2 is an exploded perspective view illustrating configurations of a cleaning body, a flange, and a tube guide that constitute the exemplary embodiment of the present disclosure.

As illustrated in FIG. 2, in the present exemplary embodiment, the flange 30 is formed to have an approximately ring-shaped flange body 31 in terms of an external appearance and a framework thereof, but the present disclosure is not necessarily limited thereto, and the flange 30 may have various shapes in accordance with a shape of the main body 10.

The flange 30 is separably coupled to the upper portion of the main body 10, and coupling channels 33 are formed in an inner surface of the flange 30. The coupling channels 33 correspond to coupling protrusions 57 of the cleaning body 50 which will be described below, and the coupling channels 33 are recessed in the inner surface of the flange 30, and serves to guide the movement of the coupling protrusions 57 during a process of coupling the flange 30 and the cleaning body 50.

Figure 3:
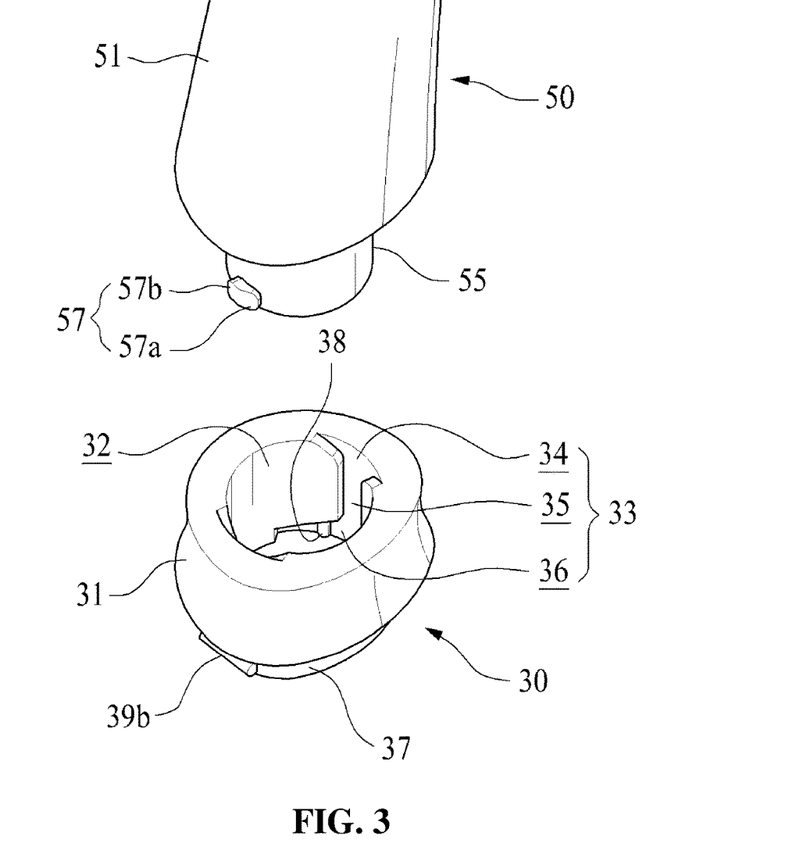
FIG. 3 is a perspective view illustrating a structure in which the cleaning body and the flange, which constitute the exemplary embodiment of the present disclosure, are coupled.
Figure 4:
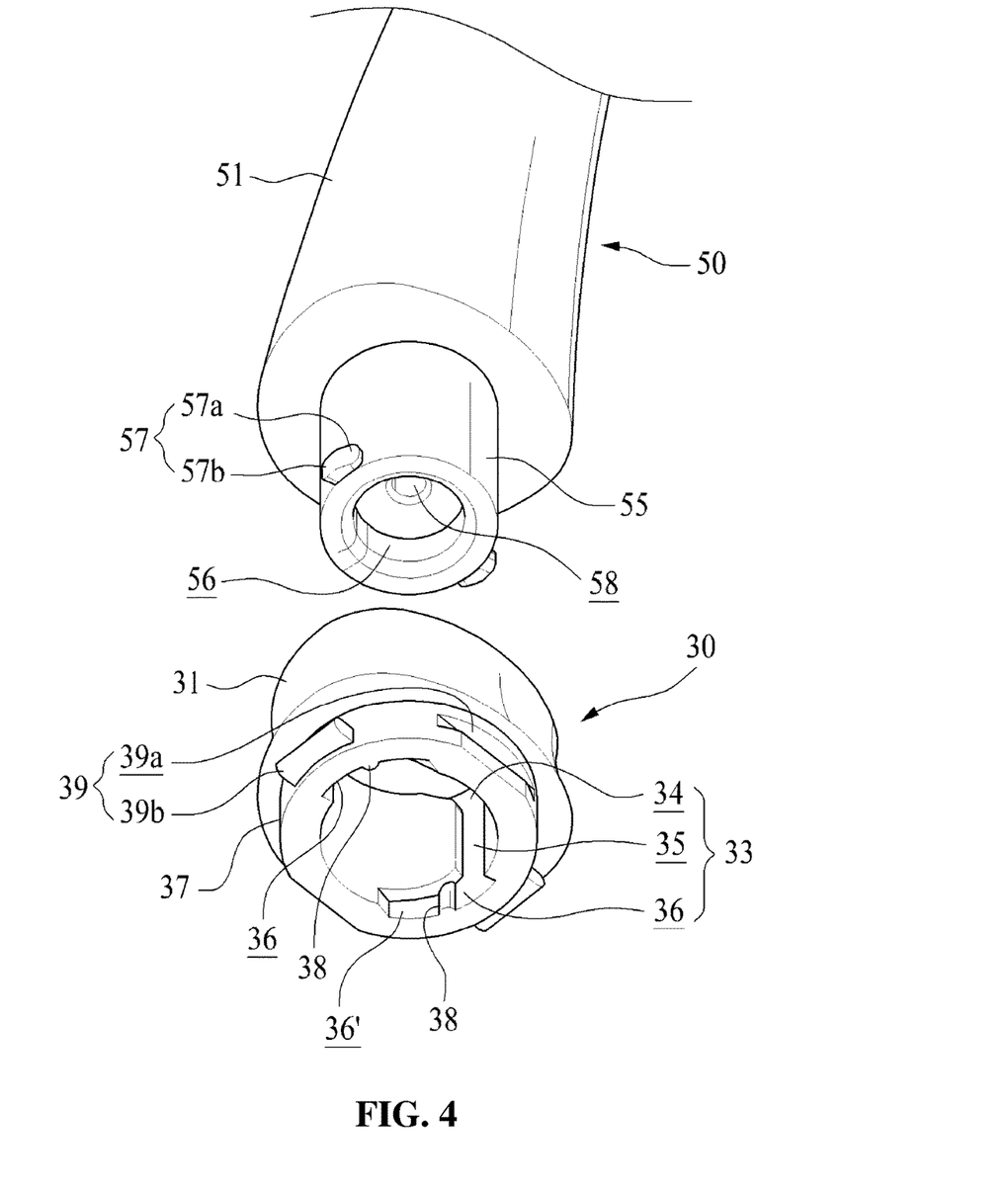
FIG. 4 is a perspective view illustrating the structure in FIG. 3 when viewed at a different angle.

A more exact shape of the coupling channel 33 is well illustrated in FIGS. 3 and 4. As illustrated in FIGS. 3 and 4, the coupling channel 33 is formed to be recessed in the inner surface of the flange 30 to a predetermined depth so that the coupling protrusion 57 may move along the coupling channel 33. More exactly, the coupling channel 33 includes an introduction portion 34, a connecting portion 35, and a rotation portion 36.

The introduction portion 34 is a portion which is opened at one end, that is, opened upward based on FIG. 2, and the connecting portion 35 is a portion which extends from the introduction portion 34 in a direction in which the main body 10 and the cleaning body 50 are coupled.

Further, the rotation portion 36 extends in a direction in which the rotation portion 36 is orthogonal to or inclined from the connecting portion 35. The reason is to allow the main body 10 and the cleaning body 50 to be coupled to each other while being rotated relative to each other about a rotation center in the longitudinal direction of the main body 10 during the process of coupling the main body 10 and the cleaning body 50.

In this case, as well illustrated in FIG. 4, a catching projection 38 protrudes at one end of the rotation portion 36. The catching projection 38 protrudes from one end of the rotation portion 36, and serves to inhibit the coupling protrusion 57 of the cleaning body 50 from climbing over the catching projection 38 and then arbitrarily moving in the opposite direction, that is, a direction in which the coupling protrusion 57 is separated. The catching projection 38 may be formed to have a curved shape so that the catching protrusion may comparatively easily climb over the catching projection 38.

Further, a seating portion 36' is formed at the other side of the rotation portion 36 based on the catching projection 38. The seating portion 36' is a portion on which the coupling protrusion 57, which has climbed over the catching projection 38, is seated when the main body 10 and the cleaning body 50 are completely coupled, and the seating portion 36' may be considered as a part of the rotation portion 36.

In this case, as illustrated in FIG. 4, an opened inlet of the introduction portion 34 is formed to have a width relatively larger than that of a portion inside the inlet. More exactly, a width of an opened portion of the introduction portion 34 increases outward, and the reason is to allow the coupling protrusion 57 to be easily inserted into the introduction portion 34.

A fastening portion 37 is provided to protrude from a lower portion of the flange 30. The fastening portion 37 has a kind of a ring shape, and protrudes downward from the flange 30, and has second fastening protruding portions 39b and second fastening recesses 39a which are formed on an outer circumferential surface of the fastening portion 37. The second fastening protruding portion 39b and the second fastening recess 39a correspond to a first fastening recess (not illustrated) and the first fastening protruding portion 15, respectively, which are formed on an inner surface of the main body 10, and as the second fastening protruding portion 39b and the second fastening recess 39a are coupled to the first fastening recess and the first fastening protruding portion 15, the flange 30 may be secured to the main body 10.

Meanwhile, the tube guide 40 is provided at a lower side of the flange 30. The tube guide 40 is provided in the main body 10 at a portion corresponding to the lower side of the flange 30, and serves to guide the path of the tube T1. That is, the tube guide 40 supports a part of the tube T1 in a state in which the tube guide 40 is fixed in the main body 10, and the tube guide 40 allows the tube T1 to be directed in the exact direction so that the tube T1 is connected with the internal fluid conduit 58 of the cleaning body 50 which will be described below.

To this end, a connecting flow path 48 is formed in the tube guide 40 so as to be elongated in one direction.

As well illustrated in FIGS. 2 and 5, in the present exemplary embodiment, the tube guide 40 includes a guide plate 41 which is supported and fixed on the inner surface of the main body 10, and the tube coupling portion 45 and a conduit insertion portion 47 which protrude in both directions from the guide plate 41, respectively.

The guide plate 41 is formed in an approximately circular plate shape, and a lateral side of the guide plate 41 is supported and fixed on the inner surface of the main body 10. Although not illustrated, the light emitting unit, which emits light, may be provided in the main body 10, and an evading portion 49 may be formed in the tube guide 40 by being recessed or opened so as to allow light emitted from the light emitting unit to pass through the evading portion 49 or allow the light emitting unit to be seated on the evading portion 49.

Here, the light emitting unit may be configured as a small-sized lighting device such as an LED, and the light emitted from the light emitting unit increases illumination intensity of the internal fluid conduit 58 and nozzles 65, thereby improving usability when the tooth cleaning device is used at night, and making an external appearance of the tooth cleaning device aesthetically attractive.

The tube coupling portion 45 protrudes from a bottom surface of the guide plate 41 and is coupled to one end of the tube T1, the conduit insertion portion 47 protrudes from an upper surface of the guide plate 41 so as to be positioned in an interior 32 of the flange 30, and at least a part of the conduit insertion portion 47 is inserted into the internal fluid conduit 58 of the cleaning body 50 when the cleaning body 50 is coupled to the flange 30.

As described above, the tube guide 40 is a connecting means that connects the tube T1 and the internal fluid conduit 58 of the cleaning body 50. In particular, as illustrated in FIG. 5, the conduit insertion portion 47 of the tube guide 40 protrudes upward and is connected with the internal fluid conduit 58 of the cleaning body 50 when a part of the conduit insertion portion 47 is superimposed with the internal fluid conduit 58 inside the flange 30. That is, a flow path is continuously formed as a coupling boss 55 of the cleaning body 50 is naturally superimposed with the conduit insertion portion 47 during the process in which the cleaning body 50 is coupled to the flange 30.

A waterproof seal S is provided on an outer surface of the conduit insertion portion 47. The waterproof seal S is provided on an outer circumferential surface of the conduit insertion portion 47, and performs a waterproof function by being compressed against both the outer surface of the conduit insertion portion 47 of the tube guide 40 and an inner surface of the coupling boss 55 of the cleaning body 50, which will be described below, during the process in which the conduit insertion portion 47 and the coupling boss 55 are coupled to each other. A non-described reference numeral 47' indicates a seating groove on which the waterproof seal S is seated.

Meanwhile, as illustrated in FIG. 5, the tube coupling portion 45 is formed such that a width thereof is decreased toward the protruding one end, and at least one coupling rib may protrude on an outer surface of the tube coupling portion 45. The reason is to increase coupling force with the tube T1 because the tube T1 is coupled to the outer surface of the tube coupling portion 45.

However, the present disclosure is not limited thereto, a single coupling rib may protrude on the outer surface of the tube coupling portion 45.

For example, although the coupling rib is not exactly illustrated in the drawings, any structure such as an unevenness shape may be applied as long as the coupling rib has a shape that protrudes from the outer surface of the tube coupling portion 45.

Next, the cleaning body 50 will be described. The cleaning body 50 is a part which is separably coupled to the main body 10, and substantially performs a cleaning function The cleaning body 50 is configured to continuously extend from the main body 10, and in the present exemplary embodiment, the cleaning body 50 is formed in a long bar shape. More exactly, a connecting bar 51, which has the internal fluid conduit 58 formed therein, defines an external appearance and a framework of the cleaning body 50, a cleaning head 60 and the coupling boss 55 are provided at both ends of the cleaning body 50, respectively.

The coupling boss 55 protrudes from a lower end of the cleaning body 50, and the coupling protrusions 57 protrude from an outer surface of the coupling boss 55 and are inserted into the coupling channels 33 of the flange 30 such that the cleaning body 50 and the main body 10 are coupled to each other.

As illustrated in FIG. 3, the coupling protrusion 57 includes a first protrusion portion 57a which relatively less protrudes from the outer surface of the coupling boss 55, and a second protrusion portion 57b which is connected with the first protrusion portion 57a and relatively further protrudes. Since the extent to which the first protrusion portion 57a protrudes is relatively small, the catching protrusion may easily climb over the aforementioned catching projection 38 of the coupling channel 33, and after the catching protrusion climbs over the catching projection 38, the second protrusion portion 57b, which protrudes further, faces the catching projection 38, such that the catching protrusion may not easily move in the opposite direction.

As illustrated in FIGS. 3 and 4, two coupling protrusions 57 are provided on the outer surface of the coupling boss 55, but the present disclosure is not necessarily limited thereto, one, or three or more coupling protrusions 57 may be provided. Of course, in this case, the coupling channels 33 also need to be formed in the flange 30 such that the number and the positions of the coupling channels 33 correspond to the coupling protrusions 57.

As illustrated in FIG. 4, one end of the internal fluid conduit 58 is exposed to an internal space 56 of the coupling boss 55, and a part of the aforementioned conduit insertion portion 47 of the tube guide 40 is inserted into one end of the internal fluid conduit 58, such that the conduit insertion portion 47 and the internal fluid conduit 58 are connected to each other.

Meanwhile, the cleaning head 60 is provided at one end of the connecting bar 51, and at least one nozzle 65 is formed on an outer surface of the cleaning head 60 so as to spray a washing liquid, which has been delivered through a tube flow path T1', the connecting flow path 48, and the internal fluid conduit 58, into the mouth, or to suck moisture in the mouth and then discharge the moisture to the outside through the internal fluid conduit 58, the connecting flow path 48, and the tube flow path T1'.

As illustrated in FIG. 2, in the present exemplary embodiment, the cleaning head 60 is formed in a cylindrical shape or a circular plate shape, but may be modified to have various sizes and shapes as long as the cleaning head 60 has a structure that may be inserted into the user's mouth.

A plurality of nozzles 65 of the cleaning head 60 may be formed on at least one of an outer circumferential surface 61 of the cleaning head 60, a front surface 62 of the cleaning head 60, and a rear surface (denoted by no reference numeral) of the cleaning head 60. For reference, FIG. 2 illustrates a state in which the plurality of nozzles 65 is formed on the outer circumferential surface 61 and the front surface 62 of the cleaning head 60, respectively.

Figure 6:
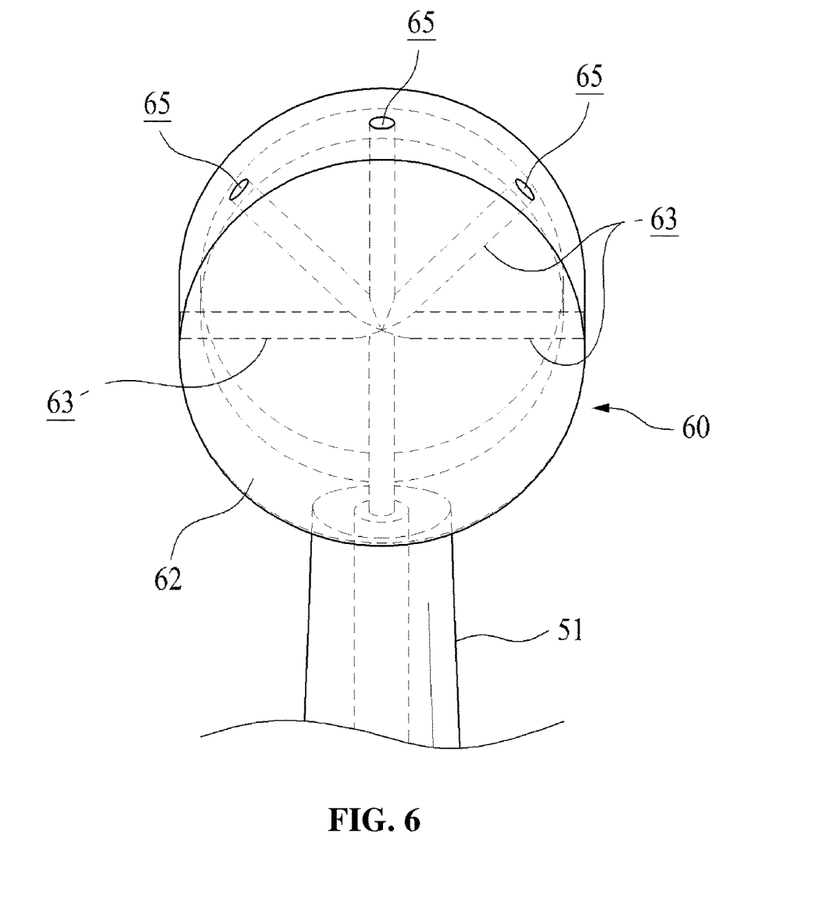
FIG. 6 is a perspective view illustrating a configuration of a cleaning head that constitutes the exemplary embodiment of the present disclosure.

As illustrated in FIG. 6, the nozzles 65 may be formed to be connected to one end of the internal fluid conduit 58, and may be formed radially toward an outer circumferential surface of the cleaning head 60. The plurality of nozzles 65 may be configured to be able to effectively spray a high-pressure washing liquid delivered from the internal fluid conduit 58. Reference numeral 63' indicates connecting channels that connect the nozzles 65 and the internal fluid conduit 58. Of course, the moisture in the mouth may be discharged to the outside through the nozzles 65 as described above.

As illustrated in FIG. 1, a brush 70 may be provided on the cleaning head 60. The brush 70 is used to brush the teeth, and configured such that a plurality of bristles is bundled. The brush 70 may be separably coupled to the cleaning head 60, or formed integrally with the cleaning head 60. The brush 70 may be coupled to the cleaning head 60 in a threaded connection manner, in a press-fit manner, or by means of an assembling protrusion (not illustrated). Of course, the brush 70 need not be necessarily provided on the cleaning head 60 and may be omitted.

Hereinafter, processes in which the tooth cleaning device having the internal fluid conduit formed therein according to the present disclosure is assembled and used will be described in detail.

Figure 7:
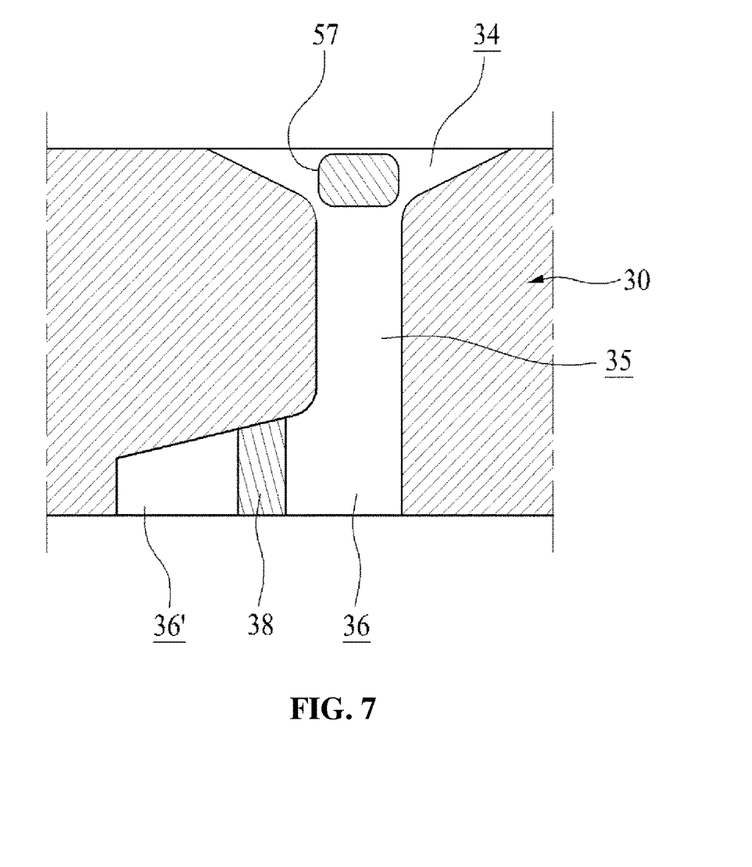
FIGS. 7 to 9 are operating state views sequentially illustrating a process in which a coupling protrusion moves while the cleaning body and the flange, which constitute the exemplary embodiment of the present disclosure, are coupled.
Figure 8:
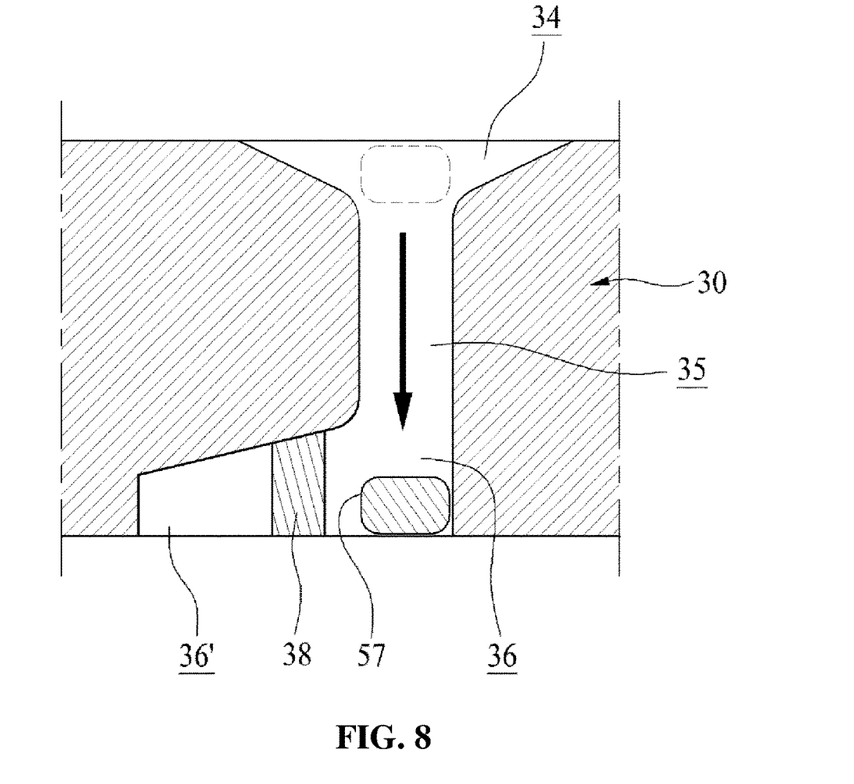
Figure 9:
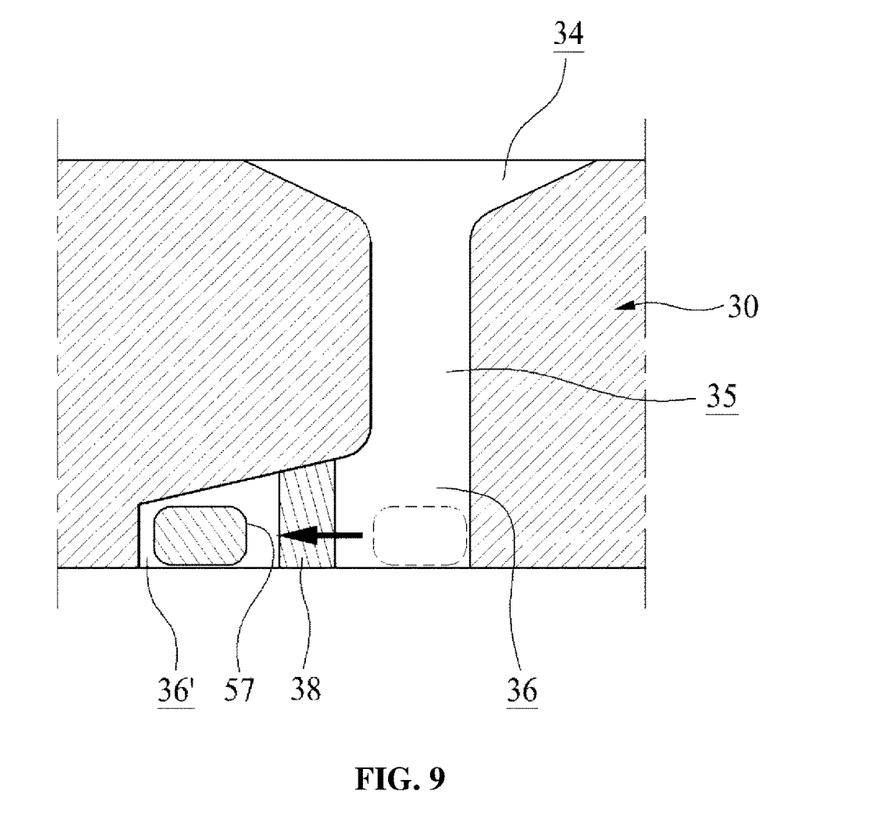

FIGS. 7 to 9 are operating state views sequentially illustrating a process in which the coupling protrusion of the cleaning body moves while the cleaning body and the flange, which constitute the exemplary embodiment of the present disclosure, are coupled.

The user cleans his/her mouth by using the cleaning head 60 of the cleaning body 50, and the cleaning head 60 may be separated from and assembled to the main body 10 for various purposes such as convenience of storing the tooth cleaning device and replacing components. First, a process in which the cleaning body 50 and the main body 10 are coupled will be described on the assumption that the cleaning body 50 and the main body 10 are separated from each other.

To couple the cleaning body 50 and the main body 10, the cleaning body 50 and the main body 10 are moved in a direction in which the cleaning body 50 and the main body 10 become close to each other in a state in which the coupling boss 55 of the cleaning body 50 is directed toward the flange 30 of the main body 10. In this case, the coupling protrusion 57 of the cleaning body 50 is directed toward the coupling channel 33 of the main body 10, and more exactly, the coupling protrusion 57 is inserted into the interior 32 of the flange 30 through the introduction portion 34 of the coupling channel 33. This state is illustrated in FIG. 7.

Further, when the main body 10 and cleaning body 50 continuously move close to each other, the coupling protrusion 57 is moved downward along the connecting portion 35 connected with the introduction portion 34 as illustrated in FIG. 8, and in this process, a part of the conduit insertion portion 47 of the tube guide 40 is inserted into the internal fluid conduit 58 provided in the coupling boss 55. This process may be naturally carried out because the conduit insertion portion 47 protrudes upward and is positioned in the interior 32 of the flange 30.

In this state, when the user rotates the main body 10 and the cleaning body 50 relative to each other about the rotation axis defined in the longitudinal direction of the main body 10, the coupling protrusion 57 climbs over the catching projection 38 of the coupling channel 33. In this process, the coupling protrusion 57 may elastically deform the flange 30 to some extent.

Further, when the coupling protrusion 57 has completely climbed over the catching projection 38, the coupling protrusion 57 is seated on the seating portion 36', and inhibited from being arbitrarily rotated in the opposite direction. The state described above is illustrated in FIG. 9.

Since the main body 10 and the cleaning body 50 are coupled by the relative rotation therebetween as described above, the main body 10 and the cleaning body 50 are not easily separated even in a case in which external force is applied in a direction in which the main body 10 and the cleaning body 50 are separated from each other. In addition, with torque generated during the relative rotation between the main body 10 and the cleaning body 50, the waterproof seal S, which is provided on the conduit insertion portion 47 of the tube guide 40, may be more easily compressed.

As a result, since the internal fluid conduit 58 and the conduit insertion portion 47 of the tube guide 40 are connected to each other inside the interior 32 of the flange 30, a single communicated flow path is provided. That is, with the process of simply assembling the main body 10 and the cleaning body 50 by rotating the main body 10 and the cleaning body 50, the flow paths may be connected to each other, and at the same time, the flow paths may be sealed.

In addition, since the tube T1 is coupled to the tube coupling portion 45 of the guide tube 40, the tube flow path T1', the connecting flow path 48, and the internal fluid conduit 58 define a single continuous flow path, and the cleaning solution may be supplied or a fluid may be discharged through the single continuous flow path.

For example, in a case in which the drive unit 100 provides high positive pressure, the cleaning solution, which has sequentially passed through the tube flow path T1', the connecting flow path 48, and the internal fluid conduit 58, is discharged to the outside, that is, into the user's mouth through the nozzles 65, thereby cleaning the user's teeth.

On the contrary, in a case in which the drive unit 100 provides high negative pressure, the liquid, which has sequentially passed through the internal fluid conduit 58, the connecting flow path 48, and the tube flow path T1', may be discharged to the outside More specifically, when the high-pressure cleaning solution is supplied from the drive unit 100, the cleaning solution moves through the tube T1 first. Further, the cleaning solution flows into the main body 10 along the tube T1, and the cleaning solution is delivered to the connecting flow path 48 of the tube guide 40 through the tube coupling portion 45 of the tube guide 40 which is coupled to the tube T1 inside the main body 10.

In this case, since the tube guide 40 is connected with the internal fluid conduit 58 of the cleaning body 50 through the conduit insertion portion 47, the cleaning solution is delivered to the internal fluid conduit 58 through the connecting flow path 48, and moves in a direction toward the cleaning head 60.

Lastly, the cleaning solution is discharged through the nozzles 65 of the cleaning head 60, and cleans the interior of the user's mouth. Of course, in a case in which the brush 70 is provided on the cleaning head 60, the user may brush his/her teeth by using the brush 70 at the same time when the cleaning solution is discharged.

In contrast, the fluid remaining in the user's mouth may be discharged in the reverse order to the aforementioned processes. That is, when the negative pressure applied from the drive unit 100 is transmitted to the nozzles 65, a fluid flowing in through the nozzles 65 is discharged to the outside through the internal fluid conduit 58, the connecting flow path 48, and the tube T1.

As the foregoing, all of the constituent elements, which constitute the exemplary embodiment according to the present disclosure, have been described as being integrally coupled or operated after being coupled, but the present disclosure is not necessarily limited to the exemplary embodiment. That is, within the scope of the object of the present disclosure, one or more of all of the constituent elements can be selectively coupled and operated. In addition, unless explicitly described to the contrary, the term "comprising", "including", or "having" will be understood to imply the inclusion of stated constituent elements but not the exclusion of any other constituent elements. All terms used herein including technical or scientific terms have the same meanings as meanings which are generally understood by those skilled in the art unless they are differently defined. Terms defined in generally used dictionary shall be construed that they have meanings matching those in the context of the related art, and shall not be construed in ideal or excessively formal meanings unless they are clearly defined in the present disclosure.

The above description is simply given for illustratively describing the technical spirit of the present disclosure, and those skilled in the art will appreciate that various modifications and changes are possible, without departing from the essential characteristic of the present disclosure. Therefore, the exemplary embodiments of the present disclosure are provided for illustrative purposes only but not intended to limit the technical concept of the present disclosure. The scope of the technical concept of the present disclosure is not limited thereto. The protective scope of the present disclosure should be construed based on the following claims, and all the technical concepts in the equivalent scope thereof should be construed as falling within the scope of the present disclosure.

For example, in the aforementioned exemplary embodiment, the tube guide 40 may be omitted, and one end of the tube T1 provided in the main body 10 may be positioned in the interior 32 of the flange 30, such that when the cleaning body 50 is coupled to the flange 30, one end of the internal fluid conduit 58 of the cleaning body 50 and one end of the tube T1 may be directly connected to each other.

What is claimed is:

1. A tooth cleaning device having an internal fluid conduit, the tooth cleaning device comprising:
    a main body having a tube and selectively connectable with a drive unit; and
    a cleaning body which is assembled to one side of the main body, and has the internal fluid conduit disposed at the cleaning body and connectable with the tube, wherein at least one nozzle is disposed to be opened at one end of the internal fluid conduit,
    wherein when the main body and the cleaning body are assembled, one end of the tube is connected to one end of the internal fluid conduit and defines a continuous flow path, a flange is coupled to the cleaning body, a tube guide is provided below the flange, and the tube guide includes a guide plate which is supported and fixed on an inner surface of the main body, a tube coupling portion which protrudes from a bottom surface of the guide plate and is coupled to one end of the tube, and a conduit insertion portion which protrudes from an upper surface of the guide plate and is positioned in the flange, and when the cleaning body is coupled to the flange, at least a part of the conduit insertion portion is inserted into the internal fluid conduit of the cleaning body.

2. The tooth cleaning device of claim 1, wherein a coupling protrusion and a coupling channel, which correspond to each other, are disposed on the cleaning body and the flange, respectively, and during a process in which the cleaning body is coupled to the flange, the coupling protrusion is guided along the coupling channel and then caught and fixed by one side of the coupling channel.

3. The tooth cleaning device of claim 2, wherein the coupling channel is disposed to be recessed in an inner surface of the flange.

4. The tooth cleaning device of claim 3, wherein when the cleaning body is coupled to the flange, one end of the internal fluid conduit of the cleaning body and one end of the tube are connected to each other.

5. The tooth cleaning device of claim 3, wherein the coupling channel includes an introduction portion which has one end opened to the outside, a connecting portion which extends from the introduction portion in a direction in which the main body and the cleaning body are coupled, and a rotation portion which extends from the connecting portion in a direction in which the rotation portion is orthogonal to or inclined from the connection portion, and a catching projection protrudes at one end of the rotation portion.

6. The tooth cleaning device of claim 1, wherein the tube is provided in the main body and is configured to be separable from the main body, and the internal fluid conduit is disposed integrally with the cleaning body.

7. The tooth cleaning device of claim 1, wherein a waterproof seal is provided on an outer surface of the conduit insertion portion.

8. The tooth cleaning device of claim 1, wherein the tube coupling portion has a shape in which a width thereof is decreased toward the protruding one end, and at least one coupling rib protrudes on an outer surface of the tube coupling portion.

9. The tooth cleaning device of claim 1, wherein a light emitting unit, which emits light, is provided in the main body, and an evading portion is disposed in the tube guide by being recessed or opened and allows light emitted from the light emitting unit to pass through the evading portion or allows the light emitting unit to be seated on the evading portion.

10. The tooth cleaning device of claim 1, wherein the cleaning body includes:
    a connecting bar which has the internal fluid conduit disposed therein;
    a cleaning head which is provided at one end of the connecting bar and has said at least one nozzle formed on an outer surface thereof; and
    a coupling boss which protrudes from the other end of the connecting bar and has a coupling protrusion provided on an outer surface thereof.

11. The tooth cleaning device of claim 10, wherein a plurality of nozzles is disposed on at least one of an outer circumferential surface, a front surface, or a rear surface of the cleaning head.

12. The tooth cleaning device of claim 10, wherein the nozzle is defined radially toward an outer circumferential surface of the cleaning head.

13. The tooth cleaning device of claim 10, wherein a brush is separably coupled to the cleaning head.

14. The tooth cleaning device of claim 1, wherein the drive unit is adapted to supply a washing liquid to the tube or to suck a liquid from the nozzle by providing negative pressure to the tube.

* * * * *